US00PP19075P2

(12) United States Plant Patent
Utecht

(10) Patent No.: US PP19,075 P2
(45) Date of Patent: Aug. 5, 2008

(54) ***PELARGONIUM* PLANT NAMED 'FISTAROL'**

(50) Latin Name: *Pelargonium×hortorum*
Varietal Denomination: Fistarol

(76) Inventor: Angelika Utecht, Hinterer Rebstock 38, Montabaur (DE), 56410

( * ) Notice: Subject to any disclaimer, the term of this patent is extended or adjusted under 35 U.S.C. 154(b) by 0 days.

(21) Appl. No.: 11/803,252

(22) Filed: May 14, 2007

(51) Int. Cl.
*A01H 5/00* (2006.01)

(52) U.S. Cl. ..... Plt./328; Plt./325

(58) Field of Classification Search ..... Plt./328
See application file for complete search history.

*Primary Examiner*—Kent L. Bell
*Assistant Examiner*—S. B. McCormick-Ewoldt
(74) *Attorney, Agent, or Firm*—Jondle & Associates, P.C.

(57) ABSTRACT

A new cultivar of *Pelargonium* particularly characterized by having light red to coral, semi-double flowers with medium-sized inflorescences, dark-green foliage with medium-sized leaves and strong zonation, a vigorous growth habit, a relatively tall, rounded, bushy and tight plant habit and an early to mid-season flowering response, is disclosed.

1 Drawing Sheet

Genus and species: *Pelargonium×hortorum.*
Variety denomination: 'Fistarol'.

BACKGROUND OF THE NEW PLANT

The present invention comprises a new and distinct cultivar of *Pelargonium,* botanically known as *Pelargonium× hortorum* and hereinafter referred to by the cultivar name 'Fistarol'. The new cultivar is a product of a planned breeding program which had the objective of creating new varieties having pink flowers, good flower color stability, medium green foliage and vigorous growth. 'Fistarol' was discovered as a seedling resulting from a cross between the proprietary female parent 'K92-1044-3' (unpatented), a *pelargonium* having deep salmon-colored flowers and the male parent, 'Fisvita' (U.S. Plant Pat. No. 15,011), a pelargonium having light salmon and white semi-double flowers. A single plant selection was chosen for further evaluation and for asexual propagation in 2003.

The new cultivar was created in 2002 in Hillscheid, Germany and has been asexually reproduced repeatedly by vegetative cuttings in Galdar, Gran Canaria, Spain, and Hillscheid, Germany, over a 4-year period. 'Fistarol' has not been observed under all possible environmental conditions, thus the phenotype may vary significantly with variations in the environment such as temperature, light intensity and day length. It has been found to retain its distinctive characteristics through successive asexual propagations.

Plant Breeder's Rights for this cultivar were applied for in Germany on Apr. 25, 2006 and in Canada on Apr. 26, 2006.

SUMMARY OF THE INVENTION

The following are the most outstanding and distinguishing characteristics of this new cultivar when grown under normal commercial practices in Hillscheid, Germany.

1. Light red to coral, semi-double flowers;
2. Medium-sized inflorescences that are initially short and later are borne well above the foliage;
3. Dark-green, nearly round, medium-sized leaves with strong zonation;

4. A vigorous growth habit and a relatively tall plant habit;
5. A rounded, bushy and moderately tight plant habit; and
6. An early to mid-season flowering response.

DESCRIPTION OF THE PHOTOGRAPH

This new *pelargonium* plant is illustrated by the accompanying photograph which shows blooms, buds, and foliage of the plant; the colors shown are as true as can be reasonably obtained by conventional photographic procedures. The photograph is of and un-pinched plant about 14-weeks-old and grown from rooted cuttings in a 14-cm pot under greenhouse conditions which approximate those generally used in commercial practice.

DESCRIPTION OF THE NEW CULTIVAR

The following detailed descriptions set forth the distinctive characteristics of 'Fistarol'. The data which define these characteristics were collected from asexual reproductions carried out in Hillscheid, Germany. The plant history was taken on 10-week-old, un-pinched plants in 12-cm pots in a greenhouse in mid-May 2006. The color readings were determined under natural light in mid-May from flowers grown in a greenhouse. Color references are to the R.H.S. Colour Chart of The Royal Horticultural Society of London (R.H.S.) (2001).

DETAILED BOTANICAL DESCRIPTION

Classification:
*Botanical.*—*Pelargonium×hortorum.*
*Common name.*—Zonal geranium.

Parentage:
*Female parent.*—'K92-1044-3' a proprietary (unpatented) pelargonium having deep salmon-colored flowers.
*Male parent.*—'Fisvita' (U.S. Plant Pat. No. 15,011) a pelargonium having light salmon and white semi-double flowers.

Plant:
*Form.*—Shrub, self-branching with a rounded shape.
*Branching habit.*—About 4.8 branches per plant.

*Height.*—12.0 cm for a 10-week-old plant (measured from base of stem to the tips of the branches, excluding the inflorescences).

*Width.*—21.6 cm for a 10-week-old plant.

*Time to produce a finished flowering plant.*—In the spring of 2006, about 7 weeks after planting of rooted cuttings, 50% of plants were flowering with at least one open flower.

*Outdoor plant performance.*—Plants continuously flower; a flower count in mid-September 2006 in Hillscheid, Germany indicated about 15–18 inflorescences per plant.

Leaves:

*Arrangement.*—Alternate; opposite at the flowering stems.

*Color, immature leaf.*—General: Deep green. Upper surface: RHS 137A to RHS 137B. Lower surface: RHS 137C.

*Color, mature leaf.*—General: Dark-green. Upper surface: RHS 137A. Lower surface: RHS 137C to RHS 137D.

*Length.*—5.5 cm to 6.0 cm.

*Width.*—8.5 cm.

*Zonation color.*—RHS 200A to RHS 200B (deep brown), relatively strong.

*Zonation diameter.*—Inner diameter of the ring is 4.0 cm to 4.5 cm, the band or belt of zonation is about 1.0 cm to 1.3 cm wide.

*Shape.*—Nearly round and only weakly kidney-shaped with nearly no lobes and with an open gap between the lowest lobes.

*Apex.*—Rounded.

*Base.*—Cordate.

*Margin.*—Bi-crenate and somewhat wavy.

*Texture.*—Upper surface is dull and velvety.

Petioles:

*Length.*—Approximately 5.0 cm to 7.0 cm.

*Diameter.*—0.3 cm.

*Color.*—RHS 143B to RHS 143C (light-green).

*Texture.*—Covered with fine pubescence.

Stems:

*Length.*—6.0 cm to 8.0 cm.

*Internode length.*—0.5 cm to 1.5 cm.

*Color.*—RHS 143B (green) and infused with RHS 174A (brown) in parts.

*Texture.*—Appears smooth, yet covered with very short pubescence.

Flower buds (just before petals unfold):

*Length.*—1.9 cm.

*Width.*—0.9 cm to 1.1 cm.

*Shape.*—Elliptical.

*Color of sepals.*—RHS 137D (green).

*Color of petals.*—RHS 41A to RHS 41B (orange-red).

Inflorescence:

*Type.*—An umbel composed of about 40 to 60 flowers and buds.

*Umbel diameter.*—9.8 cm.

*Umbel depth (height).*—5.0 cm to 5.5 cm.

*Umbel shape.*—Nearly semi-spherical.

*Lastingness of the umbel on the plant.*—About 18 days.

*Peduncle.*—Length: 11.6 cm. Diameter: 0.5 cm to 0.6 cm. Texture: Covered with dense, short glandular hair. Color: RHS 138A (light-green) and partly infused with RHS 181A (reddish) anthocyanin.

*Pedicel.*—Length: 2.5 cm. Diameter: 0.15 cm. Texture: Covered with very short glandular hair. Color: RHS 144A (green) and the upper part is RHS 181A (reddish).

Corolla:

*Form.*—Semi-double.

*Diameter.*—4.8 cm.

*Depth.*—1.5 cm to 2.0 cm.

*General color.*—Light carmine red or coral red.

*Shape.*—Round outline with the upper and lower petals roughly of the same size and basically flat cup-shaped; the inner petals may be slanting upward or somewhat irregularly directed.

*Number of petals.*—6 to 8.

*Petaloids: Present. Number:* 0 to 3. Shape: Variable; shorter and narrower than the petals and often folded or twisted. Color: Approximately RHS 43C or RHS 50B. Lastingness of the individual flowers on the plant: 7 to 8 days at 18° C. Fragrance: The umbels are not fragrant but the peduncles, pedicels and sepals when touched, give off an aromatic scent (typical for *Pelargonium zonale* or *Pelargonium× hortorum* varieties).

Petals:

*Upper petals.*—Length: 2.5 cm. Width: 1.7 cm to 1.9 cm. Color: Upper surface: Between RHS 52A and RHS 52B. Lower surface: From RHS 43C to RHS 52C. Markings: No real markings, base of petals have a more salmon hue of RHS 43B to RHS 43C.

*Lower petals.*—Length: 2.3 cm. Width: 1.9 cm to 2.1 cm. Color: Upper surface: Between RHS 52A and RHS 52B. Lower surface: Mainly RHS 43C or lighter in parts. Markings: Absent.

*Shape.*—Obovate.

*Apex.*—Rounded.

*Base.*—Broadly acute.

*Margin.*—Entire.

*Texture.*—Smooth, slightly glossy.

Sepals:

*Number.*—5.

*Length.*—10–11 mm.

*Width.*—0.4 cm for the largest upper sepal and 0.3 cm for the other sepals.

*Shape.*—Lanceolate.

*Apex.*—Acute.

*Base.*—Fused.

*Margin.*—Entire.

*Texture.*—Has short glandular hair.

*Color.*—Upper (outer) surface: RSH 144A (light-green). Lower (inner) surface: RHS 144B.

Reproductive organs:

*Androecium.*—Number of anthers: Most often 5. Filament color: Mainly RHS 49C (pale light-pink). Filament length: 0.7 cm. Pollen color: RHS 24A (light orange). Pollen amount: Moderate (typical).

*Gynoecium.*—Pistil number: 1. Pistil length: 0.8 cm. Stigma color: RHS 42A. Stigma shape: 5 to 6 lobed. Style color: RHS 49C (pale pink). Style length: 0.5 cm to 0.6 cm. Style shape: Filiform (filament-like) with the lobes of the stigma at right angles.

Fruit/seed set: No seed set observed.

Disease and insect resistance: No special observations made; average susceptibility or tolerance (not resistant to diseases and pests common to the species).

COMPARISON WITH PARENTAL AND COMMERCIAL CULTIVARS

'Fistarol' differs from the female parent 'K92-1044-3' (unpatented) in that 'Fistarol' has semi-double flowers, while 'K92-1044-3' has single-type flowers and a more compact growth habit.

'Fistarol' differs from the male (pollen) parent 'Fisvita' (U.S. Plant Pat. No. 15,011) in that 'Fistarol' has light red to coral flowers, while 'Fisvita' has light salmon and white flowers. Additionally, 'Fistarol' has dark-green leaves, while 'Fisvita' has medium green leaves.

'Fistarol' differs from the commercial comparison variety 'Fisrorose' (U.S. Plant Pat. No. 12,362) in that the flower color of 'Fistarol' has a slightly less bluish hue than 'Fisrorose'. Additionally, 'Fistarol' has dark-green leaves, while 'Fisrorose' has medium-green leaves.

'Fistarol' differs from the commercial comparison variety 'Americana Coral' (U.S. Plant Pat. No. 7,934) in that 'Fistarol' has dark-green leaves with stronger zonation. while 'Americana Coral' has larger, medium-green leaves and a more orange flower color.

I claim:

1. A new and distinct cultivar of *Pelargonium* plant as shown and described herein.

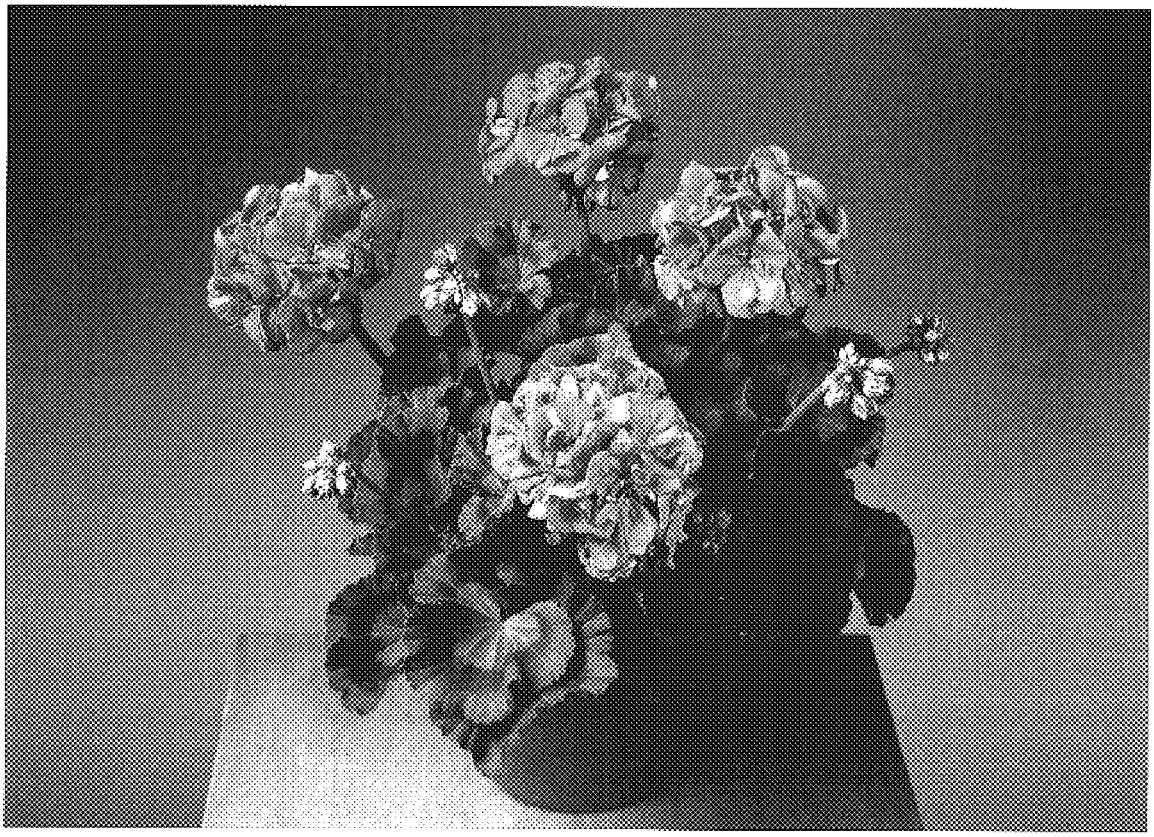

* * * * *